United States Patent [19]

Krueger

[11] 4,273,744

[45] Jun. 16, 1981

[54] DEVICE FOR AUTOMATIC ADDITION OF A CORROSION INHIBITOR TO A COOLANT SYSTEM

[75] Inventor: Robert H. Krueger, Palatine, Ill.

[73] Assignee: Borg-Warner Corporation, Chicago, Ill.

[21] Appl. No.: 85,344

[22] Filed: Oct. 16, 1979

Related U.S. Application Data

[63] Continuation of Ser. No. 964,225, Nov. 27, 1978, abandoned.

[51] Int. Cl.³ .............................................. B01D 11/02
[52] U.S. Cl. .................................... 422/265; 422/277; 165/134 R; 73/450
[58] Field of Search ............... 422/264, 265, 274, 277, 422/276; 165/134 R; 73/450, 444, 433, 434-437, 445-449

[56] References Cited

U.S. PATENT DOCUMENTS

| 745,521 | 12/1903 | Redstearn | 73/444 |
|---|---|---|---|
| 1,817,676 | 8/1931 | Christie | 73/444 |
| 1,890,900 | 12/1932 | Christie | 73/444 |
| 2,976,129 | 3/1961 | Brehler | 422/265 |
| 3,045,496 | 7/1962 | Frause | 73/450 |
| 3,390,695 | 7/1968 | King | 422/266 |
| 3,598,536 | 8/1971 | Christensen | 422/265 |
| 3,607,103 | 9/1971 | Kiefer | 422/265 |
| 3,792,979 | 2/1974 | Clinton | 422/265 |
| 3,809,150 | 5/1974 | Holmes | 165/134 |
| 3,846,078 | 11/1974 | Brett | 422/265 |

FOREIGN PATENT DOCUMENTS

| 289511 | 12/1915 | Fed. Rep. of Germany | 73/448 |
|---|---|---|---|
| 987206 | 4/1951 | France | 73/50 |
| Ad.80685 | 4/1963 | France | 73/448 |

Primary Examiner—Hiram Bernstein
Attorney, Agent, or Firm—James A. Geppert

[57] ABSTRACT

A device for the automatic addition of corrosion inhibitor into an automobile coolant system when the coolant mixture is diluted by water having an undesirable level of corrosiveness. The device is in the form of a hydrometer having a hollow stem adapted to receive a quantity of a corrosion inhibitor and having openings in the stem wall allowing contact of the liquid in the coolant system with the corrosion inhibitor when the specific gravity of the coolant liquid decreases below a predetermined level.

3 Claims, 2 Drawing Figures

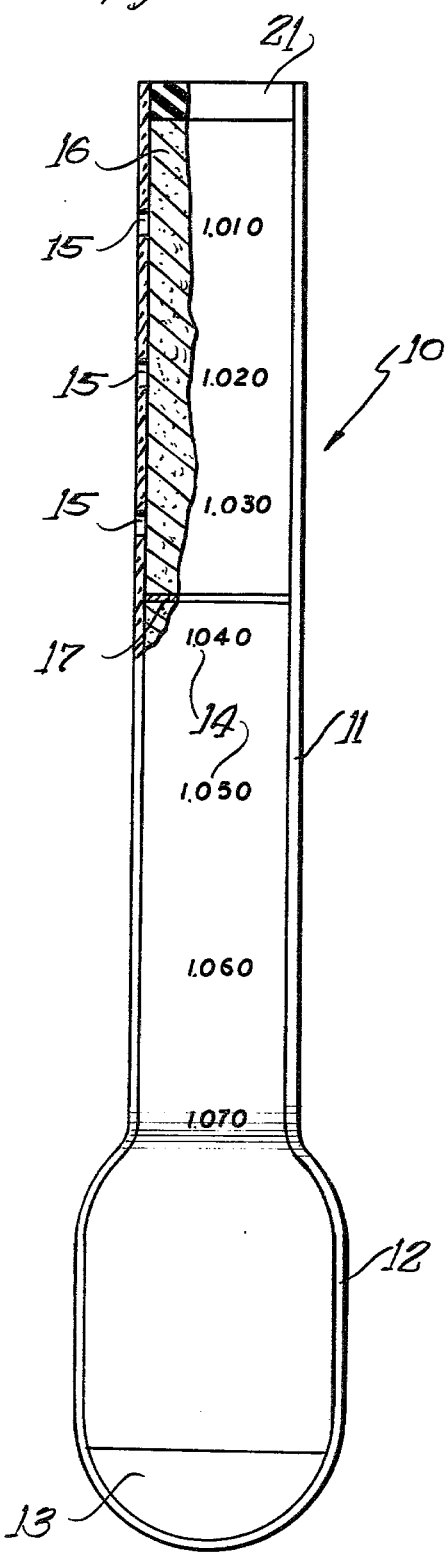
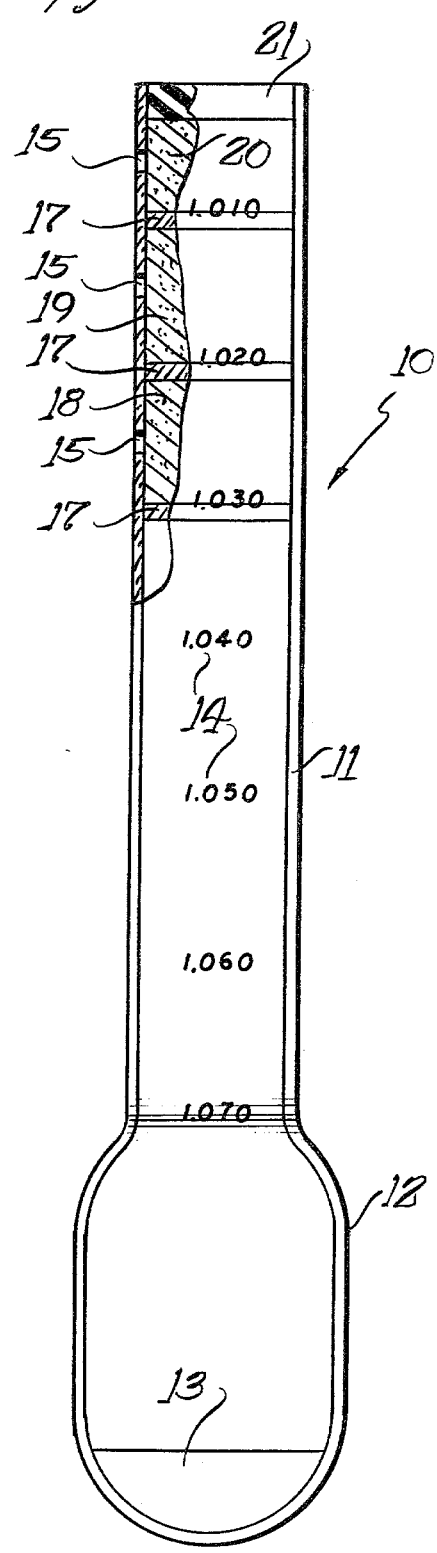

_4,273,744_

DEVICE FOR AUTOMATIC ADDITION OF A CORROSION INHIBITOR TO A COOLANT SYSTEM

This is a continuation of application Ser. No. 964,225 filed Nov. 27, 1978, now abandoned.

BACKGROUND OF THE INVENTION

The cooling system of an automotive vehicle involves the circulation of a liquid coolant through the engine block of an internal combustion engine and then through a heat exchanger or radiator by a pump operated by the engine. The coolant removes heat from the engine block during operation, and the radiator cools the heated coolant by a forced air flow through the radiator and around a plurality of tubes therein carrying the coolant. In view of the temperature extremes in many parts of the country, the conventional coolant is an approximately 50—50 mixture of ethylene glycol with water.

Presently, automotive radiators are formed of copper and/or brass, and the ethylene glycol, with a small percentage of diethylene glycol, is diluted with water to make a 50% or lower concentration of glycol depending on the desired freezing point protection. Most manufacturers or distributors of ethylene glycol also add corrosion inhibitors to the solution; which inhibitors are usually a mixture of one or more inorganic salts, such as phosphates, borates, nitrates, nitrites, silicates and arsenates, and an organic compound, such as benzotriazole, tolyltriazole, or mercaptobenzothiazole, to prevent copper corrosion. The solution is generally buffered to a pH of 8-10 to reduce iron corrosion and to neutralize any glycolic acid formed in the oxidation of ethylene glycol.

Most manufacturers of ethylene glycol recommend a maximum of one or two years' service for their antifreeze, however, the average car owner does not follow the owner's manual instructions to maintain −20° F. protection or check the coolant to see if it is rusty or dirty. Many owners only add water when the antifreeze is lost through leakage or hose breakage. In normal passenger car service, 25% of the cars require coolant system servicing after one year; and after two years, this rises to 50%. With a conventional copper-brass radiator, it is extremely important that the antifreeze mixture contains 50-55% of the correctly inhibited ethylene glycol. A reduction to 33% ethylene glycol-67% water will increase metal corrosion significantly. This is especially important with higher temperature coolant systems which are becoming more common with the increased use of emission controls.

At the present time, a concerted effort is being made by the automobile manufacturers to increase gas mileage to federally legislated standards by size and weight reduction of the automobiles. To provide weight reduction, lightweight metals and plastics are being substituted for present day heavier metal components. One such area is in the use of aluminum in place of copper and brass for automotive radiator. Aluminum provides a high heat transfer capability, however, there have been problems in dimensional stability, corrosion resistance, and in the manufacture of the aluminum structure.

In particular, the corrosion problems discussed previously are considerably accentuated for aluminum radiators and, where corrosive water is used to replace the proper ethylene glycol-water mixture due to leakage or hose breakage during operation of the vehicle, corrosion of the aluminum radiator is considerably more rapid and destructive. Thus, the present invention provides for automatic replacement of the corrosion inhibitor to avoid the corrosion problems.

SUMMARY OF THE INVENTION

The present invention comprehends the provision of a device designed to automatically add a suitable corrosion inhibitor to the coolant in an engine cooling system in the event that the operator replaces lost ethylene glycol solution with water. The device is designed as a hydrometer with a solid or liquid inhibitor in the hollow upper tube or stem above the weighted end. The hydrometer could be placed in the coolant overflow tank or, if small enough, in the radiator tank. As the specific gravity of the coolant decreases due to the addition of water, the hydrometer tube will gradually drop until the inhibitor is contacted by the coolant solution.

The present invention also comprehends the provision of a device to add corrosion inhibitor automatically to a coolant solution where a hydrometer has an upper tube with small openings therein at a level opposite the corrosion inhibitor. To provide for gradual additions, separators may be placed between levels of corrosion inhibitor so that the device will be operative over an extended period of time.

DESCRIPTION OF THE DRAWING

FIG. 1 is a side elevational view with a portion broken away of a hydrometer containing corrosion inhibitor.

FIG. 2 is a side elevational view with a portion broken away of the hydrometer with separators between inhibitor layers.

DESCRIPTION OF THE PREFERRED EMBODIMENTS

Referring more particularly to the disclosure in the drawing wherein are shown illustrative embodiments of the present invention, FIG. 1 discloses a hydrometer 10 of conventional shape with an elongated tubular stem 11 terminating in an enlarged bulbous lower end 12 wherein a suitable weight 13, such as steel shot, is located.

The tubular stem has a graduated scale 14 thereon to indicate specific gravity of the coolant and a plurality of small openings 15 in the stem generally opposite a quantity of a suitable corrosion inhibitor 16 located within the stem and resting on a glass separator 17. Assuming that the hydrometer 10 is placed in the overflow tank for the radiator (not shown) where temperatures are unlikely to exceed 200° F., at the proper specific gravity for the ethylene glycol-water mix, the stem 11 containing the corrosion inhibitor will not contact the coolant. As water is added to the coolant system to replace the loss of coolant, the hydrometer will gradually drop as the specific gravity decreases until the coolant can pass through the openings 15 to contact the inhibitor 16 and a portion of it or all of it will dissolve, depending on the contact area, which in turn depends on the water-ethylene glycol concentration.

As more specifically shown in the table, the specific gravity of the coolant will vary with concentration and temperature:

TABLE I

| Volume Percent Solution | | Freezing Pt. | Specific Gravity t°/60° F. in air | | |
|---|---|---|---|---|---|
| Ethylene Glycol | Water | °F. | 60° F. | 150° F. | 200° F. |
| 50 | 50 | −33.5 | 1.080 | 1.050 | 1.030 |
| 40 | 60 | −11.0 | 1.064 | 1.037 | 1.018 |
| 30 | 70 | 4.3 | 1.050 | 1.024 | 1.005 |
| 20 | 80 | 15.7 | 1.034 | 1.010 | 0.992 |
| 10 | 90 | 24.6 | 1.020 | 0.997 | 0.980 |
| 0 | 100 | 32.0 | 1.004 | 0.982 | 0.966 |

Considering the data in this table, assuming the hydrometer 10 is located in the overflow tank at approximately 200° F., a 50—50 mixture will have a specific gravity of 1.030 and no inhibitor will contact the coolant. However, if the specific gravity decreases to 1.020 through the addition of water, the hydrometer will drop allowing part of the solid inhibitor to dissolve. As the coolant dissolves the solid material, the weight of the hydrometer may initially increase and then decrease as the solid dissolves and is replaced by water. To overcome this, a separator 17 is located between each level 18,19,20 of inhibitor as shown in FIG. 2.

The weight of the inhibitor 16 is dependent on its solid density. Mixed powdered inhibitors can be compacted to increase their density by compression molding. For an average coolant volume of about 15 liters, requiring 0.1% inhibitor for metal protection, the weight of inhibitor needed will be 15 grams. To increase the inhibitor weight, it is necessary to increase the cross sectional area of the hydrometer. For example, to illustrate a simple case, assume the hydrometer is a cylinder which sinks to a depth "a" in water and a depth "x" in an ethylene glycol-water mixture of 50—50. Let the weight of the cylinder be m and its cross sectional area A.

Then $$mg = Aap_og = Axpg$$

where $p_o$ = density of water, p = density of ethylene glycol mixture and g = the acceleration due to gravity.

This equation shows that as m increases, A must increase for everything else to remain the same. In the hydrometers of both FIGS. 1 and 2, a rubber stopper 21 closes the open end of the stem 11.

I claim:

1. A device for the automatic addition of corrosion inhibitor to a coolant system, comprising a hydrometer having an elongated hollow stem with an enlarged weighted lower end, the hollow stem having an upper portion adapted to receive a corrosion inhibitor, said stem having a plurality of small openings opposite the corrosion inhibitor to allow ingress of liquid therein to dissolve the inhibitor when the position of the hydrometer drops relative to the liquid level as the specific gravity of the liquid decreases, said openings being spaced axially along the hollow stem in annular rows so as to dissolve layers of inhibitor sequentially, and separators in said hollow stem to divide the inhibitor into several equal portions with an annular row of openings opposite each portion.

2. A device as set forth in claim 1, in which each layer of corrosion inhibitor is compacted to increase its density.

3. A device as set forth in claim 1, in which said hollow stem is open at the upper end, and a resilient closure is inserted in the open upper end.

* * * * *